US008877125B2

(12) United States Patent
Appeaning et al.

(10) Patent No.: US 8,877,125 B2
(45) Date of Patent: Nov. 4, 2014

(54) LIGHT-ACTIVATED ANTIMICROBIAL ARTICLES AND METHODS OF USE

(75) Inventors: Maria A. Appeaning, St. Paul, MN (US); Sonja K. Belgrade, Stillwater, MN (US); Douglas E. Weiss, Golden Valley, MN (US); Narina Y. Stepanova, Inver Grove Heights, MN (US); Caroline M. Ylitalo, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 389 days.

(21) Appl. No.: 13/321,566

(22) PCT Filed: Jun. 23, 2010

(86) PCT No.: PCT/US2010/039580
§ 371 (c)(1),
(2), (4) Date: Nov. 21, 2011

(87) PCT Pub. No.: WO2011/008441
PCT Pub. Date: Jan. 20, 2011

(65) Prior Publication Data
US 2012/0070342 A1    Mar. 22, 2012

Related U.S. Application Data

(60) Provisional application No. 61/221,865, filed on Jun. 30, 2009.

(51) Int. Cl.
*A61L 2/10* (2006.01)
*A61L 9/20* (2006.01)
*A61L 2/08* (2006.01)

(52) U.S. Cl.
CPC .................. *A61L 9/205* (2013.01); *A61L 2/088* (2013.01); *A61L 2/10* (2013.01); *A61L 2209/12* (2013.01)
USPC ............................................ 422/28; 442/123

(58) Field of Classification Search
CPC .................................... A61L 2/08; A61L 2/10
USPC .................................... 422/28, 243; 442/123
See application file for complete search history.

(56) References Cited

U.S. PATENT DOCUMENTS

| 3,718,712 | A | | 2/1973 | Tushaus |
| 5,214,119 | A | | 5/1993 | Leir |
| 5,679,115 | A | * | 10/1997 | Fritzsche et al. ............ 8/444 |
| 5,738,642 | A | | 4/1998 | Heinecke |
| 5,803,086 | A | | 9/1998 | Scholz |
| 5,811,471 | A | | 9/1998 | Shanbrom |
| 5,825,543 | A | | 10/1998 | Ouderkirk |
| 5,828,488 | A | | 10/1998 | Ouderkirk |
| 5,830,526 | A | | 11/1998 | Wilson |
| 5,979,750 | A | | 11/1999 | Kindell |
| 5,985,395 | A | | 11/1999 | Comstock |
| 6,096,066 | A | | 8/2000 | Chen |
| 6,248,733 | B1 | | 6/2001 | Landgrebe |
| 6,264,976 | B1 | | 7/2001 | Heinecke |
| 6,270,952 | B1 | | 8/2001 | Cook |
| 6,361,786 | B1 | | 3/2002 | Shanbrom |
| 6,432,396 | B1 | | 8/2002 | Landgrebe |
| 6,569,521 | B1 | | 5/2003 | Sheridan |
| 6,663,978 | B1 | | 12/2003 | Olson et al. |
| 6,669,978 | B2 | | 12/2003 | Laye |
| 6,831,086 | B1 | | 12/2004 | Bernhardt |
| 7,005,394 | B1 | | 2/2006 | Ylitalo |
| 7,090,922 | B2 | | 8/2006 | Zhou et al. |
| 7,255,920 | B2 | | 8/2007 | Everaerts |
| 7,273,567 | B1 | | 9/2007 | Wellinghoff |
| 7,315,418 | B2 | | 1/2008 | DiZio |
| 7,361,474 | B2 | | 4/2008 | Siegler |
| 7,402,722 | B2 | | 7/2008 | Hill et al. |
| 2003/0228459 | A1 | | 12/2003 | Mrozinski |
| 2005/0058821 | A1 | | 3/2005 | Smith |
| 2005/0070976 | A1 | | 3/2005 | Samuel |
| 2006/0035039 | A1 | | 2/2006 | Ylitalo |
| 2006/0148915 | A1 | | 7/2006 | Floyd |
| 2006/0216523 | A1 | | 9/2006 | Takaki |
| 2007/0238660 | A1 | | 10/2007 | Michielsen |
| 2010/0048804 | A1 | | 2/2010 | Determan |
| 2010/0297406 | A1 | | 11/2010 | Schaffer |
| 2011/0020640 | A1 | | 1/2011 | Sherman |

(Continued)

FOREIGN PATENT DOCUMENTS

| CA | 1038135 | 9/1978 |
| JP | 2005-009065 | 1/2005 |
| WO | WO 94/02022 | 2/1994 |
| WO | WO 99/62822 | 12/1999 |
| WO | WO 2009/048742 | 4/2009 |
| WO | WO 2009/048743 | 4/2009 |
| WO | WO 2010/151563 | 12/2010 |

OTHER PUBLICATIONS

Bezman, "Photodynamic Inactivation of *E. coli* by Rose Bengal Immobilized on Polystyrene Beads", Photochemistry and Photobiology, 1978, vol. 28, pp. 325-329.
Lenard, "Photoinactivation of Influenza Virus Fusion and Infectivity by Rose Bengal", Photochemistry and Photobiology, 1993, vol. 58, No. 4, pp. 527-531.
U.S. Appl. No. 61/294,689 entitled, "Devices and Methods with Viscoelastic Material," filed Jan. 13, 2010.

(Continued)

*Primary Examiner* — Sean E Conley
(74) *Attorney, Agent, or Firm* — Adrian L. Pishko; Eric E. Silverman

(57) ABSTRACT

A light-activated antimicrobial article is disclosed, consisting essentially of an acridine dye covalently bonded without a linking group to a nylon material. The article may be made using electron beam processing. The article in combination with light absorbed by the acridine dye may be used to inhibit the growth of microorganisms. A photosensitive nylon material in which the acridine dye is disposed on the nylon material may also be used. Medical kits that include a light source and an article having the acridine dye are disclosed.

11 Claims, No Drawings

(56) References Cited

U.S. PATENT DOCUMENTS

| | | |
|---|---|---|
| 2011/0126968 A1 | 6/2011 | Determan |
| 2011/0134623 A1 | 6/2011 | Sherman |
| 2011/0176325 A1 | 7/2011 | Sherman |
| 2011/0253301 A1 | 10/2011 | Tachi |
| 2011/0268929 A1 | 11/2011 | Tran |

OTHER PUBLICATIONS

Lenard et al., "Photoinactivation of Influenza Virus Fusion and Infectivity by Rose Bengal," *Photochemistry and Photobiology*, vol. 58, Issue 4, pp. 527-531, 1993.

Bezman et al., "Photodynamic Inactivation of *E. coli* by Rose Bengal Immobilized on Polystyrene Beads," *Photochemistry and Photobiology*, vol. 28, Issue 3, pp. 325-329, 1978.

Handbook of Pressure Sensitive Adhesive Technology, Second Ed., edited by Donatas Satas, Van Nostrand Reinhold, New York, 1989, pp. 170-177.

Williams, "Good News! Polymer OLED Technology Is About to Come to a Sticky End," *Electronics World*, Oct. 2007, p. 40-41.

"OLED 'light bandage' helps in treatment of skin cancer," *LEDs Magazine*, Nov. 2, 2006, 2 pages.

* cited by examiner

LIGHT-ACTIVATED ANTIMICROBIAL ARTICLES AND METHODS OF USE

CROSS-REFERENCE TO RELATED APPLICATIONS

This application is a national stage filing under 35 U.S.C. 371 of PCT/US2010/039580, filed Jun. 23, 2010, which claims priority to Provisional Application No. 61/221,865, filed Jun. 30, 2009, the disclosure of which is incorporated by reference in its/their entirety herein.

FIELD

This disclosure relates to microbiology, particularly to antimicrobial articles and methods of use. Antimicrobial activity is induced by providing light to a photosensitizer.

BACKGROUND

Infectious diseases often result from invasion of the body by pathogenic microorganisms including bacteria, fungi and viruses. Over the years, many chemistries and methods have been developed to kill or inhibit the growth of pathogenic microorganisms including the development and use of antibiotics, antiviral agents and oxidizing agents. Electromagnetic radiation in many wavelength ranges has also been used. It is known that pathogenic microorganisms may be killed or their growth inhibited by exposure of the microorganisms to light in the presence of oxygen and certain photosensitizers.

SUMMARY

A light-activated antimicrobial article is disclosed herein. The light-activated antimicrobial article consists essentially of an acridine dye covalently bonded without a linking group to a nylon material. The light-activated antimicrobial article may be made by providing a photosensitive nylon material consisting of the acridine dye disposed on the nylon material, and processing the photosensitive nylon material with an electron beam.

Methods of inhibiting the growth of microorganisms are also disclosed herein. A useful method may comprise: providing a photosensitive nylon material consisting essentially of an acridine dye disposed on a nylon material, exposing the photosensitive nylon material to a microorganism, providing a light source, and activating the light source such light emitted by the light source is absorbed by the acridine dye. Another useful method may comprise: providing a light-activated antimicrobial article comprising an acridine dye covalently bonded without a linking group to a nylon material, exposing the light-activated antimicrobial article to a microorganism, providing a light source, and activating the light source such that light emitted by the light source is absorbed by the acridine dye.

Medical kits are also disclosed herein. A kit may comprise a light source, and a photosensitive nylon article consisting essentially of an acridine dye disposed on a nylon material. The kit may also comprise a light source, and a light-activated antimicrobial article consisting essentially of an acridine dye covalently bonded without a linking group to a nylon material.

DETAILED DESCRIPTION

Singlet oxygen is generated in neutrophils and macrophages for use in killing microorganisms. Superoxide dismutases, catalases, and peroxidases are defenses against radical- and reduced-oxygen species, but are not effective against singlet oxygen. A few microorganisms, such as *Cercospora*, are inherently resistant to singlet oxygen, and Gram-positive bacteria are generally more easily killed by singlet oxygen than Gram-negative bacteria. Enveloped viruses are inactivated by singlet oxygen more readily than nonenveloped viruses. It is notable that not a single documented case of acquired resistance by a bacterium, fungus, or virus to singlet oxygen is known.

The "photodynamic effect" is a term used to describe destruction of cells and microbes by photosensitizers in the presence of light. Under conditions where oxygen concentration is high and there are no reducing agents present, singlet oxygen is believed to be the destructive agent. This is the predominant mechanism (the so-called Type II mechanism) for cell destruction in cases where the photosensitizer cannot enter the cell. The Type II mechanism is known to be the predominant means of phototoxicity to *E. coli* for the xanthene dyes, such as rose bengal, for example, which upon irradiation generates reactive oxygen species such as singlet oxygen and superoxide radical anion. For photosensitizers that can pass through the lipid bilayer membrane into the interior of the cell where reducing agent concentrations, such as NADPH and glutathione, are high, the so-called Type I mechanism has been determined to be the predominant one leading to cell destruction. This mechanism involves, ultimately, the formation of a photosensitizer free radical and reactive oxygen species such as hydrogen peroxide, hydroxyl radical, and superoxide radical anion.

Some effort has been directed toward utilization of photosensitizers in free form (e.g., phthalocyanine, porphyrin, hypericin, and rose bengal) for killing bacteria and fungi and for inactivating viruses. For example, photoinactivation of influenza virus by rose bengal and light was disclosed by Lenard et al. in *Photochemistry and Photobiology*, 58, 527-531 (1993). Also, WO 94/02022 (Rabone et al.) discloses improved germicidal compositions utilizing rose bengal in photodynamic killing of microorganisms on surfaces.

Effort has also been directed toward utilization of photosensitizers in bound form in which they are relatively immobilized as compared to the free form. Photosensitizers have been covalently or ionically bonded to beads, larger molecules, oligomers, macromolecules and polymers. For example, an ionic binder was used to bind dye to woven and nonwoven fabrics as disclosed in U.S. Pat. No. 5,830,526 (Wilson et al.). Positively charged polymer carrier was used to ionically bond rose bengal such that microbes were killed in the presence of oxygen and light. Photodynamic inactivation of *E. coli* by rose bengal bonded to polystyrene beads was disclosed by Bezman et al. in *Photochemistry and Photobiology*, 28, 325-329, (1978).

Disclosed herein are light-activated antimicrobial articles and methods of using the articles. "Light-activated" refers to the ability of an article or method to induce a photodynamic effect. In this sense, light-activated means that a photosensitizer is present and transfers energy from light to generate reactive species such as singlet oxygen, hydrogen peroxide, hydroxyl radical, superoxide radical anion, photosensitizer radical and many other radicals that may be formed depending upon the particular environment of the photosensitizer. Thus, the articles and methods disclosed herein are also "light-activated" in the sense that they can become antimicrobial when subjected to light.

"Antimicrobial" refers to the ability of an article or method to kill or inhibit the growth of microorganisms such as bacteria, fungi and viruses. To "kill or inhibit the growth of"

includes limiting the presence of at least one virus, at least one bacterium, at least one fungus, or a combination thereof. To "kill or inhibit the growth of" also includes inactivation and prevention of the replication of or reducing the number of a microorganism. Different terms may be used for different microorganisms.

An article is considered to be "light-activated antimicrobial" if the article can be optically coupled to a light source such that when the light source is turned on to emit light, the article kills or inhibits the growth of some affected microorganism. Various incubation and testing methods can be used to determine the number of colony forming units per sample of an affected microorganism. The number of colony forming units killed or inhibited by the article can be determined by subjecting separate samples to light with and without the article, as long as the same or nearly the same incubation and testing methods are used. "Light-activated antimicrobial" articles result in a decrease in colony forming units, for example, in an amount of from about 80 to 100%, or from about 90 to 99.99%.

A method is considered to be "light-activated antimicrobial" if the method involves some use of the light-activated antimicrobial article and/a light source to kill or inhibit the growth of some affected microorganism (as described above for the article).

Affected microorganisms include DNA viruses, RNA viruses, RNA retroviruses, Gram-negative bacteria, Gram-positive bacteria and fungi. Affected microorganisms also include single- and double-stranded nucleic acid genomes. Affected microorganisms include negative single-stranded RNA genomes such as Orthomyxoviridae, Rhabdoviridae, Paramyxoviridae, Bunyaviridae, and Filoviridae. These are enveloped viruses. Orthomyxoviridae include the influenza viruses A, B, and C. Rhabdoviridae include rabies virus and vesicular stomatitis virus. Paramyxoviridae include parainfluenza virus of mammals (including mumps virus) and pneumovirus (such as respiratory syncytial viruses of man and cattle). Bunyaviridae include hantavirus, which causes Korean hemorrhagic fever and hantavirus pulmonary syndrome. Filoviridae include Marburg virus and Ebola virus.

Affected microorganisms include positive single-stranded RNA genomes such as Picornaviridae (non-enveloped), Retroviridae, and Togaviridae. Picornaviridae include polioviruses, coxsackieviruses, hepatitis A virus, and rhinovirus. Retroviridae include, for example, human immunodeficiency virus (HIV), simian immunodeficiency virus (SIV), and equine infectious anemia virus (EIAV). Togaviridae include Semliki Forest virus, yellow fever virus, Dengue virus, tick-borne virus, and rubella virus. Parvovirus (non-enveloped) is the only virus having a single-stranded negative-sense DNA genome. This virus primarily infects cats and dogs.

Affect microorganisms include double-stranded viruses such as Papovaviridae, Adenoviridae, Herpesviridae, Poxyiridae, and Hepadnaviridae. With the exception Herpesviridae, these viruses are non-enveloped viruses. Papovaviridae include papillomaviruses causing warts and tumors. Adenoviridae include Mastadenovirus and a variety of viruses capable of infecting the respiratory tract. Herpesviridae include herpes simplex 1 and 2, varicella zoster virus, cytomegalovirus, Epstein-Barr virus, human herpesvirus 6, antibodies to which are now known to be responsible for multiple sclerosis, and human herpesvirus 7. Poxyiridae include variola and other pox-producing viruses. Hepadnaviridae include human hepatitis B virus.

Affect microorganisms include bacteria such as *Enterococcus faecium, Staphylococcus aureus, Pseudomonas aeruginosa*, and *E. coli*. Species may be *Staphylococcus, Enterococcus, Streptococcus, Corynebacterium, Listeria, Neisseria*, and Enterobacteriaceae (which includes the genera *Escherichia, Salmonella*, and *Shigella*). The coliforms are Gram-negative rods, generally in the family Enterobacteriaceae. Some coliforms colonize the intestinal tract of humans and other animals. Some coliforms are associated with disease. Surfaces and liquids can also be contaminated with these bacteria.

Affect microorganisms include fungi such as *Candida albicans*, which causes yeast infection of the oral cavity known as thrush and an infection of the female reproductive tract known as vulvovaginitis.

Disclosed herein is a light-activated antimicrobial article consisting essentially of a photosensitizer covalently bonded without a linking group to a nylon material. The photosensitizer is preferably an acridine dye. As used herein, "consists essentially of" means that the article consists mainly of the two components, but other components that do not especially contribute to the invention or the function of the invention may be present. Typically, these other components can be used in a total amount of from 0 to about 5 wt. % relative to the total dry weight of the acridine dye.

For the light-activated antimicrobial article disclosed herein, acridine dye is covalently bonded without a linking group to nylon material. As used herein, "covalently bonded without a linking group" means that the acridine dye is directly bonded to a polyamide chain or a former polyamide chain with 0 or 1 atoms in between the covalently bonded dye and the polyamide of the nylon material. If the acridine dye is covalently bonded with 0 atoms to the nylon material, then the dye is directly bonded, with no intervening atoms, to a main chain or former main chain of the nylon material. If the acridine dye is covalently bonded with 1 atom to the nylon material, the atom may comprise carbon, oxygen or nitrogen. The article disclosed herein is distinguishable from grafted nylon polymers in which nylon is functionalized with a linking group such as acrylic acid, and then treated with a reactive species that ends up as a pendant group off the main chain polyamide of the nylon. As used herein, a "linking group" refers to a group having more than one atom.

The acridine dye can transfer energy of light emitted from a light source such that antimicrobial activity occurs. Antimicrobial activity may result from the generation of one or more reactive species such as singlet oxygen, hydrogen peroxide, hydroxyl radical, superoxide radical anion, amine-functionalized photosensitizer radical and many other radicals that may be formed depending upon the particular environment of the acridine dye.

The nylon material comprises any chemical structure referred to as nylon. In general, nylon comprises long polymer chains of repeating units linked by peptide bonds. Nylons are often named on the basis of the number of carbon atoms separating adjacent peptide bonds. Common nylon is known as nylon 6-6 which refers to hexamethylene groups between adjacent peptide bonds. Nylon may also comprise homopolymer nylon 6 or ring-opened polycaprolactam that has been polymerized.

The nylon material may exist in the form of fibers, and the Federal Trade Commission has a definition for Nylon Fiber: A manufactured fiber in which the fiber forming substance is a long-chain synthetic polyamide in which less than 85% of the amide-linkages are attached directly (—CO—NH—) to two aliphatic groups.

The nylon material may be in the form of fibers. The nylon material may be a nonwoven nylon material.

Electron beam processing or irradiating involves the production of electron beams by applying high voltage to tungsten wire filaments retained between a repeller plate and an extractor grid within a vacuum chamber maintained at about $10^{-6}$ Torr. The filaments are heated at a high current to produce electrons. The electrons are guided and accelerated by a repeller plate and an extractor grid towards a thin window of metal foil. The accelerated electrons, traveling at speeds in excess of $10^7$ meters/second (m/sec) and possessing about 10 to 300 kilo-electron volts (keV) pass out of the vacuum chamber through the foil window and penetrate whatever material is positioned immediately beyond the foil window.

Electron beam irradiating has been used for modifying various materials, including polymerizing, crosslinking, grafting and curing materials. For example, electron beam irradiating has been used to polymerize and/or crosslink various pressure-sensitive adhesives formulations coated on film substrates, and to cure various liquid coatings, such as printing inks Electron beam irradiating can be used to modify a material without the need for coating solutions. The amount of energy absorbed per unit mass, also known as the dose, is measured in units of gray and conveniently expressed as kilograys (kGy), where 1 kGy is equal to 1,000 joules per kilogram.

The light-activated antimicrobial article may be made by subjecting the nylon material to a solution of the amine-functionalized photosensitizer. The nylon material is removed from the bath and the wet sample subjected to electron beam irradiation. The article may consist of additional components but only those that do not contribute to formation of the light-activated antimicrobial article. Additional components can be present in minor amounts, e.g., less than 5 wt % of the total weight of the dried coating materials on the nylon material. The light-activated antimicrobial article is made by reaction between the photosensitizer and the nylon polyamide chains, wherein reaction is carried out by electron beam processing.

The amine-functionalized photosensitizer may be used in any amount, relative to the nylon material, that is needed to achieve a desired effect. For example, the amine-functionalized photosensitizer may be used in an amount effective in decreasing colony forming units, for example, in an amount of from about 80 to 100%. The amine-functionalized photosensitizer may be used in an amount of from about 0.01 to about 10%, or from about 0.1 to about 5%, by weight, and relative to the weight of the layer or material in which the amine-functionalized photosensitizer is used.

Electron beam irradiation of a nylon nonwoven web coated with anti-microbial dyes creates a non-leaching, antimicrobial substrate that has a variety of uses in health care and also in consumer products. The use of light activated antimicrobial dyes provides many useful properties. The antimicrobial activity could be turned on and off by controlling the amount of light on the web. The dye also provides a pleasing color, enhancing marketability. The combination of nylon, the light-activated antimicrobial dye, and the optional electron beam irradiating treatment results in an enhanced non-leaching property so the dye doesn't bleed onto other surfaces when wetted and the nylon would maintain the same amount of antimicrobial dye even after extended use.

The light source may comprise any suitable light source. The light source may comprise sunlight or ambient room lighting. Exemplary light sources also include linear light sources such as cold cathode fluorescent lamps and point light sources such as light emitting diode (LEDs). Exemplary light sources also include organic light-emitting devices (OLEDs), incandescent bulbs, fluorescent bulbs, halogen lamps, UV bulbs, infrared sources, near-infrared sources, lasers, or chemical light sources. In general, the light emitted by the light source may be visible or invisible. At least one light source may be used. For example, from 1 to about 10,000 light sources may be used. The light source may comprise a row of LEDs. The light source may comprise LEDs arranged on a circuit such that light emitted from the LEDs lights up continuously or uniformly the viscoelastic material throughout a desired area.

The light source may emit light at a desired wavelength or light having more than one wavelength within a range of wavelengths. The light source may emit light at one or more wavelengths from about 400 to about 700 nm, specifically from about 400 to about 500 nm, and more specifically from about 440 to about 460 nm. Light having a wavelength from about 440 to about 460 nm is desirable for acridine dyes, e.g., Acridine Yellow G has an absorption maximum at around 445 in aqueous solution.

The light source may be optically coupled to a viscoelastic material as described in U.S. Provisional Application No. 61/169,973 filed on Apr. 16, 2009 (64347US008, Sherman et al.), incorporated herein by reference. The viscoelastic material may be positioned relative to the light-activated antimicrobial article so that light can be extracted from the viscoelastic material and absorbed by the acridine dye, as described in U.S. Provisional Application No. 61/220,505 filed on Jun. 25, 2009 (65460US002, Appeaning et al.), incorporated herein by reference. For example, the light-activated antimicrobial article may be disposed on a viscoelastic layer, and the light source may comprise an LED pressed into an edge of the viscoelastic layer.

The light source may be powered by any suitable means. The light source may be powered using a battery, a DC power supply, an AC to DC power supply, an AC power supply, or a solar photovoltaic cell. The light source may also be powered by motion such as walking.

The light-activated antimicrobial articles disclosed herein may be provided in any number of ways. The light-activated antimicrobial articles may be provided as sheets or strips laid flat, or they can be rolled up to form a roll. The light-activated antimicrobial articles may be packaged as single items, or in multiples, in sets, etc. The light-activated antimicrobial articles may be provided in an assembled form, i.e., as part of some larger construction. The light-activated antimicrobial articles may be provided in kits wherein a light source is provided in addition to the article. The light source and article can be assembled together or separate from each other and assembled at some point by the user. The light-activated antimicrobial articles may also be provided separately such that they can be mixed and matched according to the needs of the user. The light-activated antimicrobial articles may be temporarily or permanently assembled.

Methods of inhibiting the growth of microorganisms are also disclosed herein. A useful method may comprise: providing a photosensitive nylon material consisting essentially of an acridine dye disposed on a nylon material, exposing the photosensitive nylon material to a microorganism, providing a light source, and activating the light source such that light emitted by the light source is absorbed by the acridine dye.

A useful method may comprise: providing a light-activated antimicrobial article comprising an acridine dye covalently bonded without a linking group to a nylon material, exposing the light-activated antimicrobial article to a microorganism, providing a light source, and activating the light source such that light emitted by the light source is absorbed by the acridine dye.

EXAMPLES

Sample Preparation

An 8"×11" nylon nonwoven material was placed on top of a larger sheet of PET film. Then a 0.05 wt % aqueous solution of Acridine Yellow G was pipetted onto the nylon and another identical sheet of PET film was placed over the sample. Paper towels were placed underneath this construction and a roller was used to press the dye solution evenly throughout the nylon. Excess solution was roll-pressed away onto the paper towel. Once the solution was evenly distributed, the sample was cut in half and for one half, the PET film was removed.

One half of the sample was subjected to electron beam irradiation as follows: An electron beam processor, CB-300 'Electrocurtain' (Energy Sciences, Inc.), was used. This processor uses a 12" wide PET web to convey samples through a 12" wide curtain beam of electrons. The sample construction was taped onto the web and conveyed through the processor at a speed of 20 fpm. The beam voltage was set at 300 kV and sufficient current was applied to the cathode to deliver a dose of 40 kGy to the sample. The PET film was removed and the electron beam irradiated sample was laid out to dry.

Leaching Tests

Results for leaching tests: 1"×2" samples of Acridine Yellow G with nylon, both electron beamed processed and non-electron beam processed, were placed in 20 mL vials and 5 mL of distilled water added to each. The vials were placed on a shaker for 30 mins and then left to stand on the bench for 36 days. The leached water was analyzed for dye using a UV-Vis Spectrophotometer. Dilutions of a known concentration of Acridine Yellow G were also analyzed on the UV-Vis Spectrophotometer to generate a standard curve.

The leaching liquid from the electron beam irradiated sample had a concentration of 0.741 ppm and the leaching liquid from the non-electron beam irradiated sample had a concentration of 2.11 ppm. The sample that was electron beam irradiated shows almost a 3-fold concentration reduction. These concentrations are both very low compared to the initial 0.05 wt % (500 ppm) solution that was used to treat the nylon. This shows that the dye is strongly bound to the nylon.

Antimicrobial Tests

Samples were tested in accordance with the AATCC Method 100 using D/E Neutralizing broth and 3M™ Petrifilm™ Aerobic Count Plates for enumeration. Samples were not sterilized prior to testing. Each sample (2"×2") was inoculated with 1 ml of a suspension containing approximately 1-2×10$^5$ colony forming units (CFU)/ml of an appropriate test organism. Samples are incubated at 28° C. for 24 hours. After 24 hours incubation, each sample was placed in a sterile stomacher bag and 100 ml of D/E Neutralizing Broth was added. The sample is processed for one minute in a Seward Model 400 Stomacher. Serial dilutions of 10$^0$, 10$^1$ and up to 10$^4$ were made and aerobic plate count using 3M™ Petrifilm™ Aerobic Count Plates were performed.

One set of samples was incubated in the dark and the second set was incubated with light. Total colony forming units per sample were recorded after 48 hours of incubation at 35° C.±1° C. and actual count converted log/cm$^2$. The percent reduction in microbial numbers was calculated against untreated (control) sample at 24 h. Samples were tested against *Staphylococcus aureus* (ATCC 6538) and *E. coli* (ATCC 11229).

TABLE 1

| Sample ID | S. aureus CFU/cm$^2$ Light | S. aureus Percent (%) reduction Light | S. aureus CFU/cm$^2$ Dark | S. aureus Percent (%) reduction Dark |
|---|---|---|---|---|
| After E-Beam | | | | |
| Plain Nylon Control | 22,100 | N/A | 28,000 | N/A |
| Nylon with Acridine Yellow G | 5 | 99.98 | 22,000 | 21.45 |
| No E-Beam | | | | |
| Plain Nylon Control | 6750 | N/A | 93,600 | N/A |
| Nylon with Acridine Yellow G | 5 | 99.92 | 16,200 | 82.72 |

TABLE 2

| Sample ID | E. Coli CFU/cm$^2$ Light | E. Coli Percent (%) reduction Light | E. Coli CFU/cm$^2$ Dark | E. Coli Percent (%) reduction Dark |
|---|---|---|---|---|
| After E-Beam | | | | |
| Plain Nylon Control | 1,040,000 | N/A | 5 | N/A |
| Nylon with Acridine Yellow G | 3,620,000 | N/A | 920,000 | N/A |
| No E-Beam | | | | |
| Plain Nylon Control | 1,040,000 | N/A | 5 | N/A |
| Nylon with Acridine Yellow G | 5 | 99.99 | 315,000 | N/A |

Samples of Acridine Yellow G with nylon, both electron beamed processed and non-electron beam processed, reduced gram positive bacterial load (*S. aureus*) by 3 logs when incubated in the light for 24 hours. The non-electron beam processed sample reduced gram negative bacterial load (*S. coli*) when incubated in the light for 24 hours. In general, gram negative bacteria may be more difficult to kill because these bacteria have an additional membrane as compared to gram positive bacteria.

Additional Antimicrobial Tests

Antimicrobial testing was carried out as described above. Growth in total colony forming units for each sample was recorded after 24 hour incubation with light.

TABLE 3

| Sample ID | | S. aureus Growth (log) |
|---|---|---|
| After E-Beam | | |
| Plain Nylon Control | 3.96 | 4.35 |
| Nylon with Acridine Yellow G | | 0.71 |
| Nylon with Azure A | | 2.87 |
| Nylon with Crystal Violet | | 1.01 |
| Nylon with Methylene Blue | | 2.79 |
| No E-Beam | | |
| Plain Nylon Control | 4.01 | 3.83 |
| Nylon with Acridine Yellow G | | 0.71 |
| Nylon with Azure A | | 0.71 |
| Nylon with Crystal Violet | | 0.71 |
| Nylon with Methylene Blue | | 0.71 |

What is claimed is:

1. A light-activated antimicrobial article consisting essentially of an acridine dye covalently bonded without a linking group to a nylon material, wherein when light is absorbed by the acridine dye, colony forming units of a microorganism exposed to the light-activated antimicrobial article decrease in an amount of from about 90 to 99.99%.

2. The light-activated antimicrobial article of claim 1, wherein the acridine dye is Acridine Yellow G.

3. The light-activated antimicrobial article of claim 1, wherein the nylon material is nonwoven nylon material.

4. A method of making a light-activated antimicrobial article, comprising
   providing a photosensitive nylon material consisting essentially of an acridine dye disposed on a nylon material, and
   processing the photosensitive nylon material using an electron beam such that the acridine dye is covalently bonded without a linking group to the nylon material.

5. A method for inhibiting the growth of microorganisms, comprising
   providing a photosensitive nylon material consisting essentially of an acridine dye disposed on a nylon material,
   exposing the photosensitive nylon material to a microorganism,
   providing a light source, and
   activating the light source such that light emitted by the light source is absorbed by the acridine dye and colony forming units of the microorganism decrease in an amount of from about 90 to 99.99%.

6. The method of claim 5, wherein the acridine dye in Acridine Yellow G.

7. The method of claim 5, wherein the nylon material is nonwoven nylon material.

8. A method for inhibiting the growth of microorganisms, comprising
   providing a light-activated antimicrobial article comprising an acridine dye covalently bonded without a linking group to a nylon material,
   exposing the light-activated antimicrobial article to a microorganism,
   providing a light source, and
   activating the light source such that light emitted by the light source is absorbed by the acridine dye and colony forming units of the microorganism decrease in an amount of from about 90 to 99.99%.

9. The method of claim 8, wherein the acridine dye is Acridine Yellow G.

10. The method of claim 8, wherein the nylon material is nonwoven nylon material.

11. A medical kit comprising:
    a light source, and
    a light-activated antimicrobial article consisting essentially of an acridine dye covalently bonded without a linking group to a nylon material, wherein when light is absorbed by the acridine dye, colony forming units of a microorganism exposed to the light-activated antimicrobial article decrease in an amount of from about 90 to 99.99%.

* * * * *

UNITED STATES PATENT AND TRADEMARK OFFICE
CERTIFICATE OF CORRECTION

PATENT NO. : 8,877,125 B2  
APPLICATION NO. : 13/321566  
DATED : November 4, 2014  
INVENTOR(S) : Maria Appeaning Page 1 of 1

It is certified that error appears in the above-identified patent and that said Letters Patent is hereby corrected as shown below:

In the Specification

Column 3,  
Lines 53-54, delete "Poxyiridae," and insert -- Poxviridae, --.  
Line 62, delete "Poxyiridae," and insert -- Poxviridae, --.

Column 5,  
Line 17, delete "inks" and insert -- inks. --.

Signed and Sealed this  
Twenty-first Day of April, 2015

Michelle K. Lee  
*Director of the United States Patent and Trademark Office*